(12) United States Patent
Cavalli et al.

(10) Patent No.: US 8,950,237 B2
(45) Date of Patent: Feb. 10, 2015

(54) GAS ANALYZER SYSTEM CONFIGURED TO DETERMINE THE CONCENTRATION OF A REFRIGERANT GAS AND/OR THE CONCENTRATION OF CONTAMINANT GASES IN AN AUTOMOTIVE AIR CONDITIONING SYSTEM

(75) Inventors: Manuele Cavalli, Musestre di Roncade (IT); Roberto Giudici, Breda di Piave (IT)

(73) Assignee: Texa S.p.A. (IT)

( * ) Notice: Subject to any disclaimer, the term of this patent is extended or adjusted under 35 U.S.C. 154(b) by 0 days.

(21) Appl. No.: 13/483,294

(22) Filed: May 30, 2012

(65) Prior Publication Data
US 2012/0312047 A1    Dec. 13, 2012

(30) Foreign Application Priority Data
May 30, 2011    (IT) .............................. TV2011A0073

(51) Int. Cl.
*G01N 30/02*    (2006.01)
*B60H 1/00*    (2006.01)
(Continued)

(52) U.S. Cl.
CPC ............ *B60H 1/00585* (2013.01); *G01N 21/63* (2013.01); *G01N 21/3504* (2013.01);
(Continued)

(58) Field of Classification Search
CPC ...... A61K 2300/00; C10G 1/10; B29C 66/71; B29K 2023/065; C04B 18/023; H01M 10/0525; C08L 67/04; C08L 2666/02; A61M 5/1452; A61B 5/14532
USPC ............................................. 73/1.02, 335.11
See application file for complete search history.

(56) References Cited

U.S. PATENT DOCUMENTS 4,649,711 A * 3/1987 Sibley et al. .................... 62/129
5,524,477 A * 6/1996 Wajid ........................... 73/24.05
(Continued)

FOREIGN PATENT DOCUMENTS

EP    2375194 A1 * 10/2011

OTHER PUBLICATIONS

Search Report from Italian Patent Appln. No. TV20110073 (Jan. 18, 2012).

*Primary Examiner* — Peter Macchiarolo
*Assistant Examiner* — Mohammed Keramet-Amircola
(74) *Attorney, Agent, or Firm* — Matthew A. Pequignot; Pequignot + Myers LLC (57) ABSTRACT

A gas analyzer system to determine the concentration of gases in an automotive air conditioning system comprising: an infrared multi-detector device equipped with a gas analysis chamber; an emitter source emitting infrared radiation in the analysis chamber; infrared multi-detectors generating an electrical measurement quantity based on the absorption of radiation by the gas; a suction pump creating a depression inside the analysis chamber; and an electronic control unit determining a main automotive refrigerant gas concentration and the contaminant gases concentration, based on electrical measurement quantities provided by the multi-detectors and a reference electrical quantity. The control unit controls the pump to suck the gases in the analysis chamber until a condition of absence of gases is achieved, wherein the internal pressure of the chamber reaches a minimum pressure, and then determines the reference electrical quantity, based on the electrical quantity generated in the condition of absence of gases.

10 Claims, 3 Drawing Sheets

(51) Int. Cl.
*G01N 21/63* (2006.01)
*G01N 21/3504* (2014.01)
*F25B 45/00* (2006.01)
*F25B 49/00* (2006.01)

(52) U.S. Cl.
CPC ............... *F25B45/00* (2013.01); *Y02T 10/88* (2013.01); *F25B 49/005* (2013.01); *F25B 2345/005* (2013.01); *F25B 2400/08* (2013.01)

USPC ......... 73/23.2; 73/23.35; 73/31.04; 73/23.42; 73/114.74

(56) References Cited

U.S. PATENT DOCUMENTS 5,610,398 A * 3/1997 Anderson et al. ........ 250/339.12
2005/0012042 A1 * 1/2005 Weckstrom et al. .......... 250/343

* cited by examiner

GAS ANALYZER SYSTEM CONFIGURED TO DETERMINE THE CONCENTRATION OF A REFRIGERANT GAS AND/OR THE CONCENTRATION OF CONTAMINANT GASES IN AN AUTOMOTIVE AIR CONDITIONING SYSTEM

RELATED APPLICATION DATA

This application claims priority to Italian Patent Application No. TV2011A 000073, filed on May 30, 2011. The entirety of such application is hereby incorporated by reference.

FIELD OF INVENTION

The present invention relates to a gas analyzer system configured to determine the concentration of a refrigerant gas and/or the concentration of contaminant gases in an automotive air conditioning system.

BACKGROUND OF THE INVENTION

It is known that the efficiency of an automotive air conditioning system depends on the refrigerant gas used, which in addition to obviously corresponding to a specific type of refrigerant gas specified by the vehicle manufacturer, must have a certain level of "purity" with regard to other types of gas, henceforth indicated as "contaminant gases".

In the real world, it often happens that the refrigerant gas in the system becomes impure, i.e., it becomes accidentally mixed with a quantity, albeit minimal, of contaminant gases. Refrigerant gas contamination can be intrinsically present from source, i.e., present in the refrigerant gas used when first charging the air conditioning system, or it can happen after the initial charging, for example, due to service operations on the automotive air conditioning system or the substitution of one type of refrigerant gas with another type of refrigerant gas.

Nowadays, the above-mentioned risk of contamination is a very real problem in the automotive industry, as regulations have been introduced that require the refrigerant gas R-134 currently used in automotive air conditioning systems to be replaced with a new type of refrigerant gas R-1234yf, different from the old one.

To this end, the need has arisen in the automotive industry to make gas analyzer systems configured to determine, with a certain accuracy, the type and actual concentration of the refrigerant gas actually in the automotive air conditioning system, in order to establish whether the latter meets the above-indicated regulations.

Some of the currently known refrigerant gas analyzer systems function using NDIR (Non Dispersive InfraRed) technology and normally include: an inlet terminal that can be connected to a connector on the low pressure system to receive the refrigerant fluid in the gaseous state at a constant predetermined pressure; a gas analysis chamber; a pressure reduction device, arranged between the inlet terminal and the gas analysis chamber to supply the refrigerant gas to the latter at a reduced pressure with respect to the pressure of the gas leaving the low pressure circuit, typically a pressure higher than the ambient pressure; an infrared radiation emission source configured to emit a radiation beam in the infrared frequency band inside the gas analysis chamber; an infrared multi-detector device configured to generate an electrical signal having an electrical quantity that is indicative of the radiation absorbed by the gas in certain frequency bands; and an electronic control circuit to determine the concentration of the refrigerant gas inside the analysis chamber, based on the electrical quantity generated by the multi-detector device.

The above-described gas analyzer systems are typically configured to perform an initial automatic calibration, during which the electronic control circuit determines a reference electrical quantity, normally a voltage, which is indicative of a condition of absence of gas in the analysis chamber and which is associated with an absolute reference value, in particular, a null gas concentration, henceforth indicated as the zero reference. The reference electrical quantity associated with the zero reference is then used in calculating the refrigerant gas concentration. In the case in point, the automatic calibration is performed by feeding air taken from the outside environment through an active-carbon filter and into the analysis chamber, generating the radiation beam in the chamber and assigning the electrical quantity generated by the multi-detector device in the presence of ambient air in the analysis chamber to the reference electrical quantity.

Unfortunately, the calculation of the reference electrical quantity performed by means of the above-described initial automatic calibration suffers from an intrinsic error based on the presence of contaminant gases in the outside ambient air used for reference. Laboratory tests performed by the applicant have in fact demonstrated that air taken from the outside environment, even if filtered using an active-carbon filter, is not pure, but contains significant percentages of contaminant gases such as, for example, $CO_2$, CO etc. Thus, the presence of contaminant gases contained in the ambient air during calibration introduces an intrinsic error into the reference electrical quantity and, in consequence, in the calculated concentration of the refrigerant gas, thus causing a reduction in the accuracy of the analysis.

It is also known that for the purposes of increasing the precision in measuring the concentration of the refrigerant gas, the need has lately arisen to be able to determine with high precision, not just the percentage of the high-concentration gas, namely the refrigerant gas, but also the percentage of "low concentration" gases, or rather the contaminant gases, so as to have comprehensive information on the composition of the gas present in the automotive air conditioning system.

However, this need has not yet been satisfied due to certain technical problems that have remained unsolved up to now and basically derive from the difficulty of sizing the analysis chamber in an adequate manner, both for the analysis of the refrigerant gases present with high concentrations and for the analysis of contaminant gases present in low concentrations.

In particular, laboratory tests performed by the applicant on analyzer systems of the above-described type, in which it is contemplated maintaining the gas in the analysis chamber at a pressure substantially equal to the ambient pressure, have demonstrated that increasing the containment volume of the gas inside the analysis chamber causes, on one hand, a corresponding increase in the precision of measuring gases present in low concentrations, but, on the other hand, a progressive reduction in the precision of measuring the gas with a high concentration, a typical condition faced in the case of analysing refrigerant gases, up to the point of arriving to a state where analysis is impossible. In fact, the presence of a high refrigerant gas concentration in a particularly "large" chamber volume causes high absorption of energy from the radiated beam, which if expanded beyond a certain volume threshold induces a saturation condition in the electrical signal generated by the multi-detector device that renders analysis of the gas impossible.

Conversely, by keeping the pressure of the gas in the analysis chamber substantially equal to the ambient pressure and reducing the internal volume of the analysis chamber, greater precision is obtained in measuring the high-concentration gas, as the number of moles of gas analysed is reduced, in this way avoiding the risk of saturation for the multi-detector device, but at the same time, the precision in measuring the low-concentration gases is reduced because the number of moles able to absorb the radiation is extremely low and becomes undetectable by the multi-detector device.

Lastly, the above described analyzer systems are configured to discharge the analysed gas contained in the analysis chamber into the outside environment, with all of the consequences that this entails from the standpoint of environmental pollution.

SUMMARY OF THE INVENTION

The applicant has carried out in-depth research with the aim of identifying a solution that enables achieving the following specific objectives:

increasing both the precision of measuring the concentration of gases present in high concentrations, in particular the refrigerant gas, and the precision of measuring the concentration of contaminant gases present in low concentrations, using a same compact analysis chamber in order to reduce costs and bulk;

increasing the precision in determining the reference electrical quantity associated with the zero reference during the automatic calibration of the analyzer system; and eliminating the environmental impact caused by emission of the gases after analysis.

The subject of the present invention is therefore that of providing a solution that enables the above-indicated objectives to be achieved.

This objective is achieved by the present invention in so far as it relates to a gas analyzer system configured to determine the concentration of a refrigerant gas and/or contaminant gases in an automotive air conditioning system, as defined in the appended claims.

Preferably, the present invention also relates to a refrigerant gas recharging/recovery station for an automotive air conditioning system embodied according to claim 10.

BRIEF DESCRIPTION OF THE DRAWINGS

The present invention will now be described with reference to the attached drawings, which illustrate a non-limitative embodiment, where.

DETAILED DESCRIPTION OF THE INVENTION

The present invention will now be described in detail with reference to the attached figures to enable a skilled person to produce and use it. Various modifications to the described embodiments will be immediately evident to skilled persons and the generic principles described can be applied to other embodiments and applications without however leaving the scope of protection of the present invention, as defined in the appended claims. Therefore, the present invention should not be considered as limited to the embodiments described and shown herein, but be accorded the broadest scope of protection commensurate with the characteristics described and claimed herein.

Figure 1:
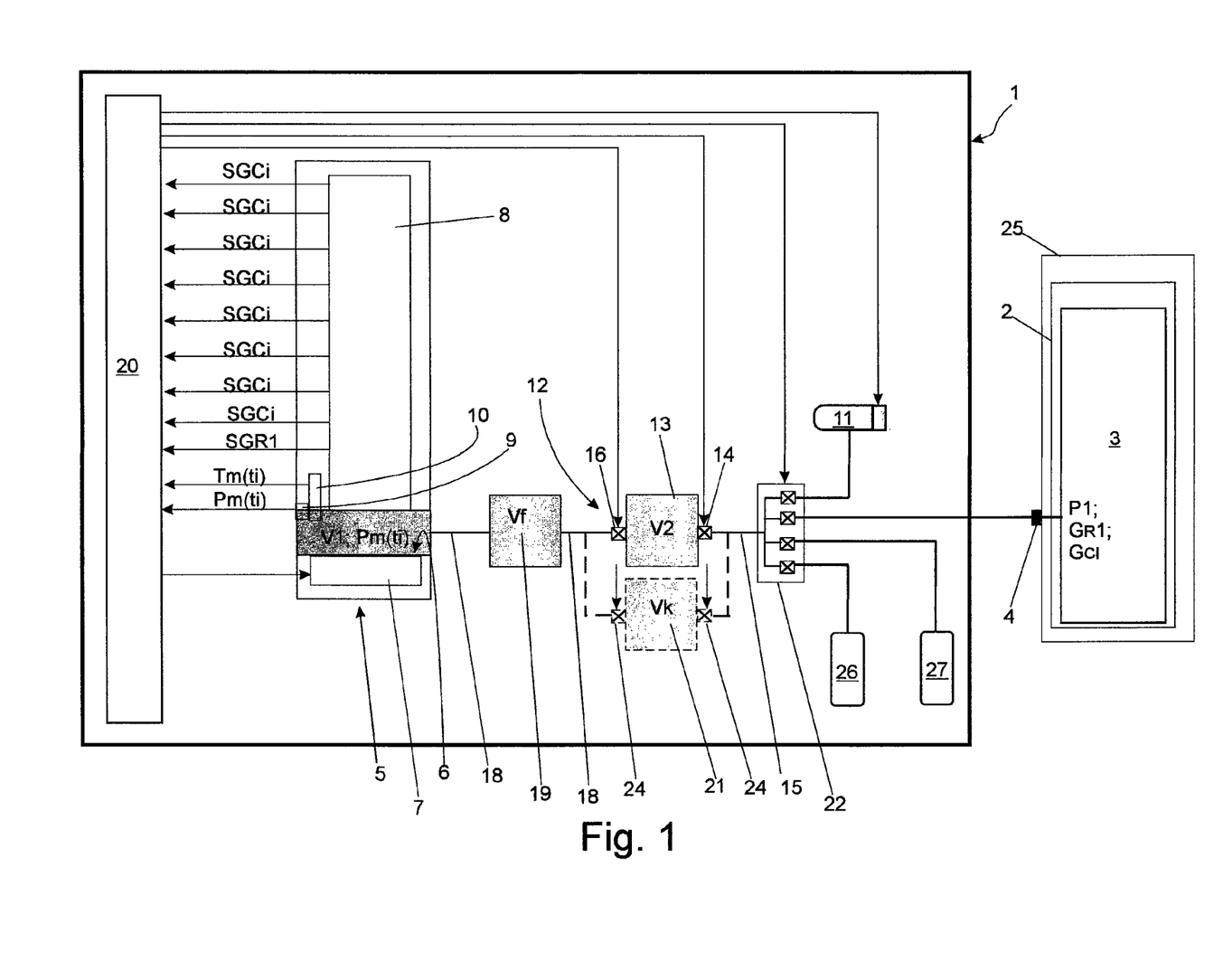
FIG. 1 schematically shows a gas analyzer system, made according to the principles of the present invention.

With reference to FIG. 1, reference numeral 1 illustrates a gas analyzer system in its entirety, configured to determine the concentration of a refrigerant gas and/or the concentration of contaminant gases in an automotive air conditioning system 2.

The automotive air conditioning system 2 is of known type and will not be described further, other than specifying that it is installed on board a motor vehicle 25 and comprises a coolant circuit 3, inside at least part of which a predetermined type of refrigerant gas circulates at low pressure, namely at a main pressure P1 preferably between approximately 3 and 15 Bar (equivalent to the vapour pressure of the gas in question at a variable temperature between approximately 5 and 50 degrees centigrade). The air conditioning system 2 has an external low pressure connector/terminal 4 through which it is possible to exchange the predetermined refrigerant gas with the coolant circuit 3, or rather, it is possible to perform refrigerant gas recharging on, or recovery from, the air conditioning system 2.

The analyzer system 1 is provided with: an infrared multi-detector device 5, which comprises an analysis chamber 6 designed to receive and hold the gas to be analyzed and having an internal gas containment volume V1; an infrared emitter device 7, which is coupled to the analysis chamber 6 and is configured to emit a radiation beam, having specific wavelengths in the infrared spectrum, inside the analysis chamber 6 so as to pass through the gas contained therein; and a series of sensors or infrared multi-detectors 8, which are coupled to the analysis chamber 6, preferably on the opposite side from the infrared emitter device 7, and are configured to measure the concentration of a predetermined series of gases present in the analysis chamber 6, based on the radiation energy variations in the absorption frequency bands of the predetermined gases.

Preferably, the infrared multi-detectors 8 are configured to measure: the concentration of a predetermined main refrigerant gas GR1 present with a high concentration in the analysis chamber 6, or rather, having a concentration (calculated, for example, as a percentage of the total volume of gas analyzed) greater than approximately 95% of the total amount of gas within the analysis chamber 6; and the concentration of one or more "contaminant" gases GCi (i is between 1 and K), possibly present in low concentrations in the analysis chamber 6, or rather, each having a concentration (calculated, for example, as a percentage) lower than approximately 5% of the overall volume of the gas contained in the analysis chamber 6.

The refrigerant gas GR1 could correspond to a first type of automotive refrigerant gas, while the contaminant gases GCi could correspond to other types of automotive refrigerant gases different from the refrigerant gas GR1, or to other types of gases not corresponding to automotive refrigerant gases. For example, the refrigerant gas GR1 could correspond to an R-1234 type automotive refrigerant gas, while the contaminant gases GCi could correspond to R-134, or R-22, or R-407, or R-152 type gases and/or "non-refrigerant" gas types such as, for example, $CO_2$, CH, HC, $O_2$, $CH_3$, $CH_4$, etc. However, it is evident that according to the various embodiments, the automotive refrigerant gas GR1 could correspond to any type of automotive refrigerant gas distinct from gas R-1234, such as, for example, gas R-134, or gas R-22, or gas R-407, or gas R-152, or a similar refrigerant gas.

The infrared multi-detectors 8 are configured to provide electrical output signals, the electrical quantities (current or voltage) of which are indicative of the concentrations of the gases detected in the analysis chamber 6. In particular, the electrical quantity of an electrical signal SGR1 generated by the infrared multi-detectors 8 is indicative of the concentration of the predetermined main automotive refrigerant gas GR1, while the electrical quantities of electrical signals SCi generated by the infrared multi-detectors 8 are each indicative of the concentration of a corresponding contaminant gas GCi inside the analysis chamber 6.

The analyzer system 1 further comprises a pressure sensor 9 and preferably, but not necessarily, a temperature sensor 10, opportunely coupled to the analysis chamber 6, to respectively measure the pressure Pm and the temperature Tm of the gas held within it.

With reference to FIG. 1, the gas analyzer system 1 further comprises: a suction pump 11, preferably a vacuum pump, which is connected to the analysis chamber 6 and is able, upon command, to generate a vacuum in the latter, or a "depression" with respect to ambient pressure, so as to evacuate the gases contained therein; and a pressure regulator device 12, which is configure to increase, upon command, the pressure of the gas inside the analysis chamber 6, according to predetermined pressure steps ΔPi, starting from a minimum pressure associated with the pressure inside the analysis chamber 6 in the vacuum condition, up to maximum pressure lower than or equal to the main pressure P1 of the gas inside the air conditioning system 2.

According to one possible embodiment, the pressure regulator device 12 can comprise, for example, an electric pressure reduction device (not shown) that is configured to take in gas from the air conditioning system 2 and adjust its outlet pressure based on a control signal.

According to a preferred embodiment shown in FIG. 1, the pressure regulator device 12 conveniently comprises: a dosage chamber 13 having an internal gas containment volume V2 and having a first terminal connected, through an electrically controlled shut-off valve 14, for example a solenoid valve, to a first end of a duct 15 suitable, in turn, for being connected by its second end to the external connector/terminal of the vehicle air conditioning system 2; and a second terminal connected, through an electrically controlled shut-off valve 16, for example a solenoid valve, to an end of a duct 18 connected, in turn, by its other end to the analysis chamber 6.

Referring to the example shown in FIG. 1, the analyzer system 1 further comprises a changeover unit 22 comprising, for example, a multi-way shut-off valve, which is able, upon command, to connect the second end of duct 15, alternatively, to the pump 11, or to the external connector 4 of the automotive air conditioning system 2, or to a first reservoir 26, or to a second reservoir 27.

The analyzer system 1 further comprises an electronic control unit 20, which is electrically connected to: the pump 11 and the infrared emitter device 7 to control their switching on and off; the infrared multi-detectors 8 to receive the electrical signal SGR1 indicative of the detected concentration of the main refrigerant gas GR1 and the electrical signals SGCi indicative of the contaminant gases detected in the analysis chamber 6; the pressure sensor 9 and temperature sensor 10 from which to receive, at time ti, the measured pressure Pm(ti) and temperature Tm(ti); the shut-off valves 14 and 16 to control their opening/closing; and the multi-way valve, to alternatively command connection of duct 15 to the pump 11, or to the external connector 4 of the air conditioning system 2, or to reservoir 26 or reservoir 27.

The electronic control unit 20 is configured to: control the pressure regulator device 12 to make the pressure of the gases in the analysis chamber 6 progressively increase, at predetermined time intervals, according to a "step-like" growth trend in which each pressure step, at a certain time ti, corresponds to a predetermined pressure variation ΔP.

The electronic control unit 20 is further configured so that at each pressure variation ΔP: it samples, by means of the infrared multi-detector device 5, the concentration of the main gas GR1 and/or the concentration of each of the contaminant gases GCi inside the analysis chamber 6, so as to obtain a plurality of samples CGR1(Pm(ti)) and CGCi(Pm(ti)), where Pm(ti) is the pressure set/measured at time ti in the analysis chamber 6; and it processes the samples CGR1(Pm(ti)) and CGCi(Pm(ti)) in order to determine, on the basis of these samples, the actual concentration of the refrigerant gas and the actual concentrations of the contaminant gases.

As will be described in detail further on, according to a preferred embodiment, the electronic control unit 20 is configured to advantageously adjust the pressure of the gases in the analysis chamber 6 in an "indirect" manner, namely through the controlled alteration of the volume occupied by the gases. Basically, provision is made to store the gases taken from the system 2 in the dosage chamber 13 at a pressure P1 and in a volume V2, and to subsequently place the dosage chamber 13 in communication with the analysis chamber 6, so as to make the previously dosed, or "quantized" (in terms of pressure and volume and therefore of moles), gas expand in a controlled manner from a volume V2 (and a pressure P1) to an overall volume substantially defined by the approximate sum of the internal volumes of the dosage chamber 13 and the analysis chamber 6 (V1+V2), so as to cause (due to the known ideal gas law PV=nRT) a reduction in pressure of the gas in the analysis chamber 6 (pressure Pm(ti)).

Figure 2:
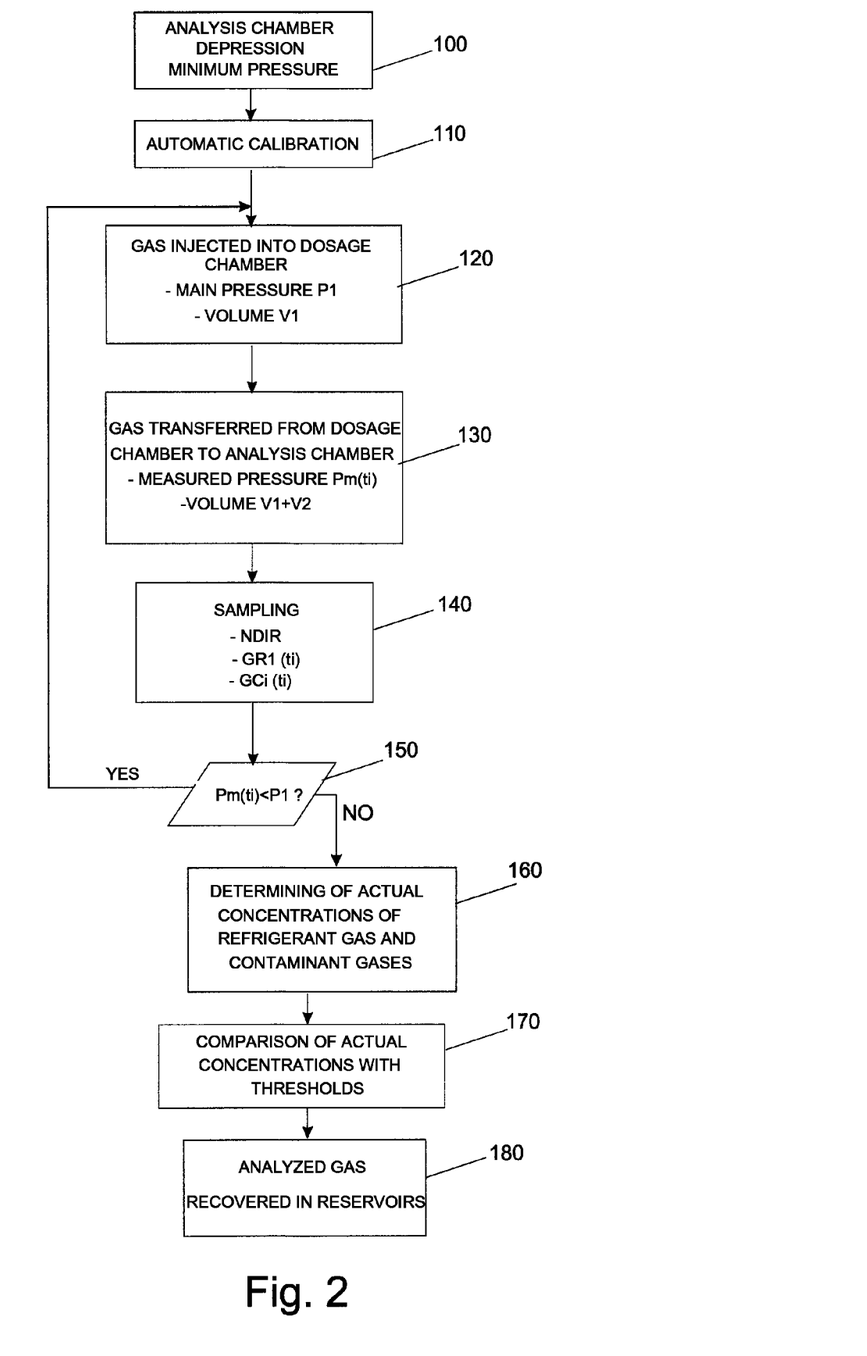
FIG. 2 is a flowchart of the operations performed by the analysis system shown in FIG. 1.

The operations implemented by the analyzer system 1 in determining the actual concentration of the refrigerant gas and/or the actual concentrations of the contaminant gases are indicated in FIG. 2.

In particular, (block 100) the electronic control unit 20 is configured to control the opening of valves 14 and 16, control the multi-way valve to connect the pump 11 to duct 15 and to operate the pump 11 in order to suck the gases contained in the analysis chamber 6 until a condition of absence of gas in the analysis chamber 6 is achieved, in which the internal pressure of the latter approximately reaches a minimum vacuum pressure. The minimum vacuum pressure can be between approximately 0 and $5*10^{-3}$ Bar, preferably $2.5*10^{-3}$ Bar. In other words, the electronic control unit 20 operates the pump 11 to create an approximate vacuum condition, or depression, in the analysis chamber 6, in the dosage chamber 13 and in ducts 15 and 18 so as to bring them to a predetermined minimum pressure corresponding to the vacuum pressure, lower than the main pressure P1. In this step, the pump 11 advantageously evacuates the analysis chamber 6, the dosage chamber 13 and ducts 15 and 18 from any trace of gas, in this way bringing about their complete cleaning.

The electronic control unit 20 is configured to advantageously carry out a calibration of its reference electrical quantity, associated with the condition of absence of gas inside the gas analysis chamber 6 (block 110). In the case in point, the electronic control unit 20 determines the reference electrical quantity based on the electrical quantity generated by the infrared multi-detector device 5 in the condition of absence of gas.

In fact, the complete cleaning of the gas analysis chamber 6 enables the analyzer system 1 to associate the reference electrical quantity, for example the voltage value V0 of the electrical signal SCGR1 generated by the infrared multi-detectors 8, with a null gas concentration (zero reference used for subsequent measurements) in a conveniently accurate manner.

The pressure adjustment contemplates that, at each time ti, the electronic control unit 20 operates to close shut-off valve 16 in order to isolate the dosage chamber 13 from the analysis chamber 6, and controls the multi-way valve so as to connect duct 15 to connector 4, thereby placing the dosage chamber 13 in communication with the air conditioning system 2. In this step, the gas in air conditioning system 2 expands inside the dosage chamber 13, due to the difference between the minimum pressure and the main pressure P1 (present in the dosage chamber 13 and in the system 2 respectively), until a state of equilibrium is achieved, in which the pressure of the gas inside the latter reaches the main pressure P1.

At this point, or rather, once the state of equilibrium has been reached, the electronic control unit 20 closes shut-off valve 14 so as to completely separate or isolate the dosage chamber 13 from the air conditioning system 2, in this way completing the dosing or "quantization" of the gas in the dosage chamber 13. In fact, in this step, the dosage chamber 13 contains a predetermined quantity of gas received from the system 2, as the gas is contained in a predetermined volume V2 and has a predetermined pressure P1 (block 120).

After completing the dosing of the gas in the dosage chamber 13, the electronic control unit 20 controls the opening of shut-off valve 16 in order to connect the dosage chamber 13 to the analysis chamber 6 and so make the gas inside the latter expand, thanks to the pressure difference between the main pressure P1 in the dosage chamber 13 and the pressure in the analysis chamber 6, which in the first step corresponds to the minimum pressure, while in the subsequent steps (times ti) it corresponds to the measurement pressure (Pm(ti)) (block 130).

It should be clarified that, in this step, the gas contained in the dosage chamber 13 expands, passing from volume V2 of the dosage chamber 13 to volume V1+V2, in this way causing an increase in pressure from the minimum pressure to the measurement pressure $Pm(ti)=P0+*\Delta P(ti)$ (i between 1 and N), where P0 is the minimum pressure, while the value of Pm(ti) can be determined on the basis of the known ideal gas state equation PV=nRT through the following equation $Pm(ti)=P1*V2/(V1+V2)=P1*\Delta V=P0+\Delta P(ti)$.

The discrete adjustment of the pressure of the gas inside the analysis chamber 6 is therefore conveniently performed in an indirect manner thanks to a controlled variation $\Delta V$ in the expansion volume of the gas, during the analysis, which passes from a charged condition, in which the gas is kept confined in the dosage chamber 13 in a predetermined volume V2 and at a predetermined pressure P1, to a condition of injection into the analysis chamber 6, in which the gas expands to occupy a volume V1+V2>V1 and increases the pressure in the analysis chamber 6 by amount $\Delta P(ti)$.

It should be clarified that pressure step $\Delta P$ can be varied by opportunely changing the gas containment volume during analysis. To this end, the analyzer system 1 could include one or more auxiliary dosage chambers 21 having volumes Vk connectable in series or in parallel to the main dosage chamber 13 (as shown in FIG. 1) and activatable by means of the solenoid valves 24 in an identical manner to that of the valves 14 and 16 connected to the main dosage chamber 13. In this case, the electronic control unit 20 can vary the pressure step $\Delta P$ used in one or more auxiliary dosage chambers 21 in addition to the dosage chamber 13, such that:

$$Pm(ti) = P1*V2 \Big/ \left(\left(\sum_{k=0}^{K=M} V_K\right) + V1\right) = P1*\Delta V = Pm(t_{i-1}) + \Delta P$$

According to one possible embodiment shown in FIG. 1, the analyzer system 1 preferably, but not necessarily, comprises a filter 19 arranged along duct 18 to filter impurities in the refrigerant gas, such as water for example. The filter 19 can be structured to have a gas containment volume equal to VF. In this case, in the absence of auxiliary dosage chambers 21, the pressure variation $\Delta P(ti)$ could also be determined by means of the contribution of volume VF through the following relation:

$Pm(ti)=P1*V2/(V1+V2+VF)=P1*\Delta V=Pm(t_{i-1})+\Delta P$.

When the gases in the analysis chamber 6 have reached the above-described state of equilibrium, the electronic control unit 20 samples the concentration of the main refrigerant gas GR1 and the concentrations of the contaminant gases GCi inside the analysis chamber 6 (block 140) on the basis of the electrical signals generated by the infrared multi-detector device 5, and measures the pressure Pm(ti) and preferably the temperature Tm(ti) (block 140).

In the case where the pressure Pm(ti) is lower than the main pressure P1 (YES exit from block 150), the electronic control unit 20 may perform the operations described in blocks 120, 130 and 140 again. Instead, if the pressure Pm(ti) is approximately equal to the main pressure P1 (NO exit from block 150), the electronic control unit 20 may determine the concentration of the main refrigerant gas GR1 and/or the concentrations of the contaminant gases GCi on the basis of the refrigerant gas samples CGR1(Pm(ti)) and the samples of the contaminant gases CGCi(Pm(ti)).

In particular, the above-described operations implemented in blocks 120, 130 and 140 can be repeated N times by the analyzer system 1 to obtain N samples of the concentration of the main refrigerant gas CGR1 and N samples of the concentrations of the contaminant gases CGCi.

It should be clarified that the progressive increase of pressure Pm(ti) in the analysis chamber 6 takes place progressively and sequentially for N times until a state of equilibrium occurs (block 150), in which the measured pressure Pm(ti) approximately reaches the main pressure P1 of the dosage chamber 13 and, in consequence, the gas in the dosage chamber 13 is no longer able to freely expand inside the analysis chamber 6.

According to a preferred embodiment, the electronic control unit 20 is configured to determine, on one hand, the actual concentration of the refrigerant gas GR1 based on the samples CGR1(Pm(ti)) taken in a first range of pressures lower than a first predetermined pressure threshold and, on the other, the actual concentration of the contaminant gases GCi based on the concentration samples of contaminant gases CGCi(Pm (ti)) taken in second range of pressures higher than a second predetermined pressure threshold, which in turn is higher than the first predetermined pressure threshold (block 160).

The first range of pressures can be between the minimum pressure associated with the vacuum pressure and the first predetermined pressure threshold, while the second range of pressures can be between the second predetermined pressure threshold and the main pressure P1.

Preferably, but not necessarily, the first predetermined pressure threshold could have a value, for example, lower than approximately $500*10^{-3}$ Bar, while the second predetermined pressure threshold could, for example, have a value higher than approximately $500*10^{-3}$ Bar.

According to one possible embodiment, the electronic control unit 20 is configured to determine the actual concentration of the main refrigerant gas based on a sample CGR1 (Pms) taken at a predetermined reference pressure Pms contained in the first discrete range of pressures, and determine the actual concentration of each of the contaminant gases based on the gas samples CGCi(Pmki) taken at predetermined reference pressures Pmki contained in the second range of pressures.

According to one possible embodiment, the electronic control unit 20 is configured to determine the actual concentration of the main refrigerant gas based on a weighted average of the samples CGR1(Pm(ti)) taken in the first discrete range of pressures and, at the same time, determine the actual concentration of each contaminant gas GCi based on a weighted average of the concentration samples CGCi(Pm(ti)) of the contaminant gas GCi, taken in the second discrete range of pressures.

According to a different embodiment, the electronic control unit 20 is configured to determine the actual concentration of the main refrigerant gas based on the largest (for example, having the largest percentage) of the samples CGR1 (Pm(ti)) taken in the first discrete range of pressures and, at the same time, determine the actual concentration for each contaminant gas GCi based on the largest of the contaminant gas samples CGCi(Pm(ti)) taken in the second range of pressures.

Regarding the foregoing, it is opportune to clarify that the electronic control unit 20 is configured to determine the concentration of the refrigerant gas and/or contaminant gas in the analysis chamber 6 by means of a radiation absorption function $F(V0/Vm(ti))$, where $V0$ is the reference quantity, for example a voltage of the electrical signal generated by the infrared multi-detectors 5 during the automatic calibration, while $Vm(ti)$ is the voltage of the electrical signal generated by the infrared multi-detectors 8 at time ti.

Preferably, but not necessarily, the radiation absorption function can correspond, for example, to the Beer-Lambert equation, where $F(V0/Vm(ti))=-\log(V0/Vm(ti))$.

The electronic control unit 20 is also configured to compare the actual concentration of the main refrigerant gas with a predetermined refrigerant gas threshold concentration and generate a warning message/signal on the basis of the outcome of the comparison. For example, the warning signal could be generated when the actual concentration of the main refrigerant gas is below a predetermined refrigerant gas concentration.

The electronic control unit 20 can also be configured to compare the actual concentration of each of the contaminant gases with a corresponding contaminant gas concentration threshold and generate a warning message/signal on the basis of the outcome of the comparisons. For example, the warning signals could be generated when the actual concentration of one or more contaminant gases is higher than the respective concentration threshold.

The electronic control unit 20 can also be configured to operate the pump 11 and/or the shut-off valves 14 and 15 and the multi-way valve in order to transfer the refrigerant gas contained in the analysis chamber 6 into the first 26, or alternatively, the second refrigerant gas recovery reservoir 27, depending on the outcome of the comparison, and so advantageously recover the gas.

In particular, if the actual concentration of the refrigerant gas and/or the actual concentrations of the contaminant gases satisfy the predetermined conditions set with the corresponding concentration thresholds, the electronic control unit 20 considers the refrigerant gas to meet the required specifications and conveniently recovers it in the first recovery reservoir 26. Instead, if the actual concentration of the refrigerant gas and/or the actual concentrations of the contaminant gases do not satisfy the above-stated conditions set with the concentration thresholds, the electronic control unit 20 considers the refrigerant gas to be "off-specification" and conveniently recovers it in the second recovery reservoir 27.

Figure 3:
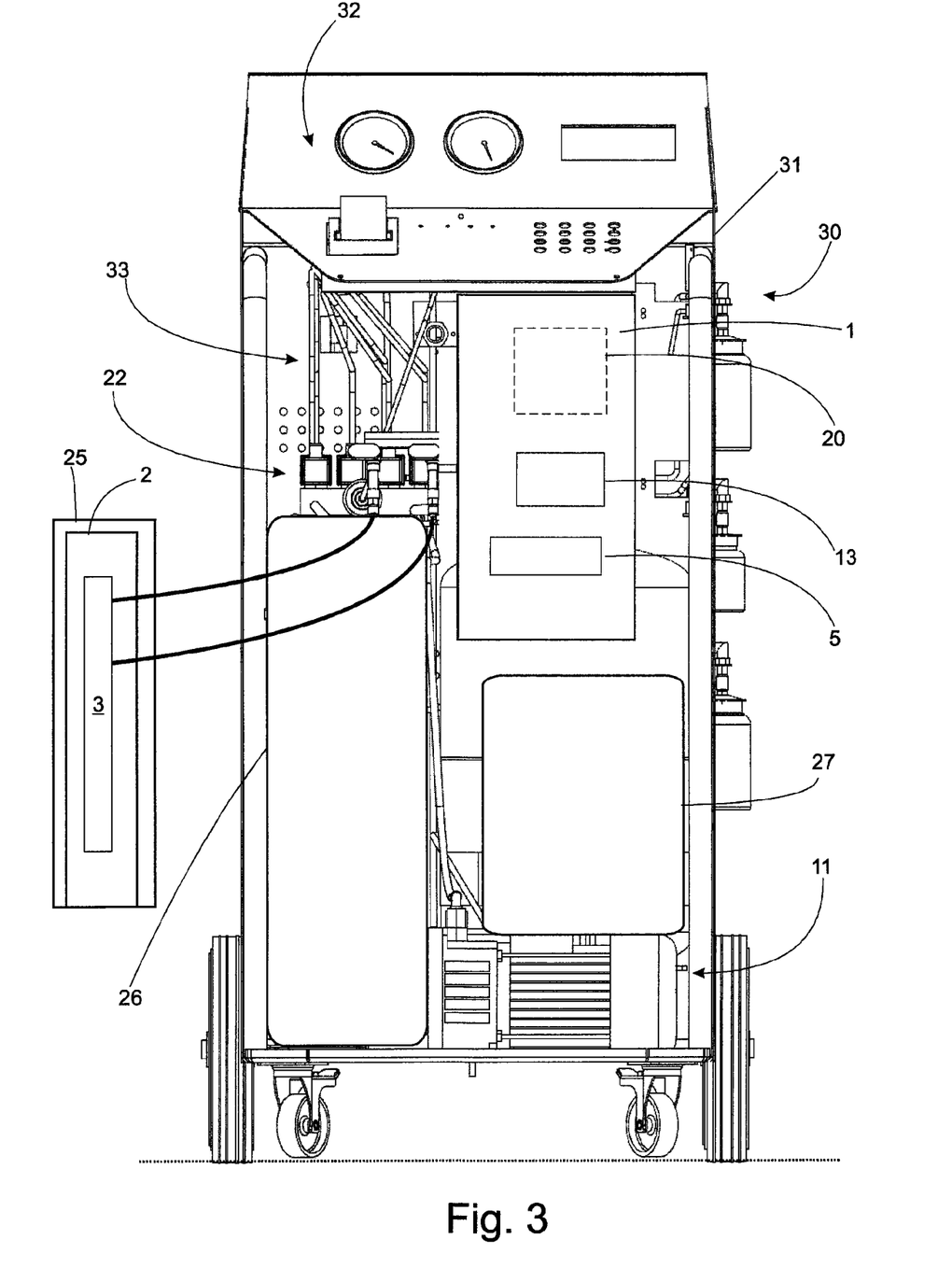
FIG. 3 schematically shows a refrigerant gas recharging/recovery station for an automotive air conditioning system equipped with the gas analyzer system shown in FIG. 1.

With reference to FIG. 3, the above-described analyzer system 1 can be advantageously included in a refrigerant gas recharging/recovery station or machine 30, of the type comprising a wheeled housing 31 to allow the station 30 to be moved and, preferably, a user control interface 32, the electronic control unit 20, the first and the second refrigerant gas holding reservoirs 26 and 27, the vacuum pump 11, the changeover unit 22 and a refrigerant recovery unit 33 structured to hold the refrigerant gas in the first 26 or, alternatively, in the second refrigerant gas holding reservoir 27, as described above.

The electronic control unit 20, the pump 11 and the changeover unit 22 can be advantageously shared by the station and the gas analyzer system 1 so as to carry out both the above-described operations contemplated for the analyzer system 1 and the refrigerant gas recovery/recharging operations on the system 2 with the recharging/recovery station 30.

Nevertheless, it is obvious that according to a different possible embodiment, the analyzer system 1 could be independent of the recharging/recovery station or machine, but communicate with the latter through a known communication system.

The advantages of the above-described gas analyzer system are the following. Firstly, the complete evacuation of gas from the analysis chamber performed during the automatic calibration enables determining a correct reference quantity, as it is associated with a real condition of absence of gas in the analysis chamber. The precision of calculation of the reference quantity results in a consequent increase in precision of the actual gas concentration measurements, especially when the calculation uses an equation associated with radiation absorption in which the reference quantity is employed.

The "discrete" pressure adjustment of the gas in the analysis chamber obtained through the use of the dosage chamber enable, on one hand, to limit manufacturing costs for the system and, on the other, to enable the size of the analysis chamber to be reduced, thereby achieving a reduction in the overall bulk of the system. In fact, thanks to the use of the dosage chamber, separate from, but communicating with the analysis chamber 6 upon command, it is possible to reduce the size of the latter, in this way ensuring the absence of saturation conditions for the infrared multi-detector device during analysis of the high-concentration gas.

In addition, the system differentiates between a refrigerant gas "meeting the specifications" and an "off-specification" gas, and conveniently and completely automatically recovers them in separate, specially provided reservoirs, without causing any discharge into the outside environment.

Finally, it is understood that changes and modifications can be made to the system and to the station described and illustrated herein without departing from the scope of the present invention defined in the appended claims.

The invention claimed is:

1. A gas analyzer system configured to determine the concentration of the gases in an automotive air conditioning system, the gas analyzer system comprising:
   a gas analysis chamber configured to contain gases to be analyzed;

emitting means so configured and connected to said gas analyzer system so as to emit infrared radiation into said analysis chamber;

infrared multi-detecting means configured to generate electrical measurement quantities based on detected absorption of said infrared radiation by gas within said analysis chamber;

pumping means being so configured and connected to said analysis chamber, so that when said pumping means is operated, said pumping means generates a depression within said analysis chamber;

an electronic control means configured, in a calibration mode, to:

a) control said pumping means to suck gases contained in the analysis chamber out of said analysis chamber until a condition of absence of gases in the analysis chamber is obtained, said condition being in which the internal pressure in the analysis chamber reaches a predetermined minimum pressure;

b) switch on said emitting means, so that said emitting means emits infrared radiation in said analysis chamber when said condition of absence of gases in said analysis chamber has been achieved; and c) determine an electrical reference quantity, based on an electrical quantity generated by said infrared multi-detecting means upon detecting absorption of said infrared radiation within said analysis chamber, in said condition of absence of gases;

said electronic control means further being configured to:

take at least one electrical measurement quantity provided by said infrared multi-detecting means when analyzing a main automotive refrigerant gas; and determine the concentration of the main automotive refrigerant gas and the concentration of contaminant gases contained in said automotive air conditioning system, based on said at least one electrical measurement quantity and said electrical reference quantity.

2. The analyzer system according to claim 1, wherein the refrigerant gas in said automotive air conditioning system is at a first pressure, higher than said minimum pressure;

said analyzer system further comprising:

pressure adjusting means configured to receive the gas from said automotive air conditioning system at the first pressure and supply it to said analysis chamber at a measurement pressure higher than said minimum pressure and lower than or equal to said first pressure;

said electronic control means also being configured to:

control said pressure adjusting means to progressively increase the measurement pressure of the gas inside the analysis chamber, according to predetermined pressure steps, from said minimum pressure up to a maximum pressure, lower than or equal to said first pressure;

sample, at every pressure variation, through said infrared multi-detector means, the concentration of said main refrigerant gas and the concentration of each of the contaminant gases inside the analysis chamber to obtain a plurality of concentration samples of refrigerant gas and a plurality of concentration samples of the contaminant gases;

determine the actual concentration of the refrigerant gas and the actual concentrations of the contaminant gases based on the concentration samples of the refrigerant gas and the concentration samples of the contaminant gases, respectively.

3. The analyzer system according to claim 2, wherein said electronic control means are also configured to determine the actual concentration of the refrigerant gas based on the concentration samples taken in a first discrete range of pressures lower than a first predetermined pressure threshold, and determine the actual concentration of the contaminant gases based on the concentration samples of contaminant gases taken in a second discrete range of pressures higher than a second predetermined pressure threshold, which is in turn higher than said first predetermined pressure threshold.

4. The analyzer system according to claim 3, wherein said electronic control means are configured to determine the actual concentration of the main refrigerant gas based on a sample taken at a predetermined reference pressure included in the first discrete range of pressures, and determine the actual concentration of each contaminant gas based on the samples taken at predetermined reference pressures included in the second range of pressures.

5. The analyzer system according to claim 3, wherein said electronic control means are configured to determine the actual concentration of the main refrigerant gas based on a weighted average of the samples taken in the first discrete range of pressures and, at the same time, determine the actual concentration of the contaminant gases based on a weighted average of the concentration samples of contaminant gases taken in the second discrete range of pressures.

6. The analyzer system according to claim 2, wherein said pressure adjusting means comprises at least one gas dosage chamber having a second containing volume and having a first terminal receiving the refrigerant gas from said automotive air conditioning system through a first duct and a second terminal providing said refrigerant gas to said analysis chamber through a second duct;

first and second intercepting means of the gas arranged along the first and the second duct, respectively;

said electronic control means being configured to vary the measurement pressure of the gas within the analysis chamber, according to predetermined pressure steps, by sequentially performing the following operations for each pressure step:

closing and opening said second and first intercepting means, respectively, to cause the refrigerant gas of the automotive air conditioning system to freely flow into the dosage chamber until a balance condition is achieved, in which the pressure and volume of the gas in the dosage chamber correspond to the first pressure and to the second volume, respectively, so as to dose the gas to be analyzed; and subsequently closing and opening said first and, respectively, second intercepting means to cause the refrigerant gas dosed in the dosage chamber to freely expand in the analysis chamber until a balance condition is achieved, in which the volume of the refrigerant gas is approximately equal to the sum of the first volume of said analysis chamber and at least the second volume.

7. The analyzer system according to claim 6, wherein said electronic control means are configured to adjust the measurement pressure of the gas in the analysis chamber based on the following equation $Pm(ti)=P1(V2/(V1+V2))$, where $Pm(ti)$ is the measurement pressure, $P1$ is the main pressure, $V2$ is the second volume and $V1$ is the first volume.

8. The analyzer system according to claim 1, wherein said electronic control means are also configured to:

compare said actual concentration of the refrigerant gas with a predetermined refrigerant concentration threshold; and/or compare the actual concentration of each contaminant gas with a corresponding predetermined concentration threshold for the contaminant gas; and generate a warning message/signal on the basis of the outcome of said comparisons.

9. The analyzer system according to claim 8, comprising at least a first and at least a second reservoir for recovering the refrigerant gas;

said electronic control means also being configured to control said pumping means and said first and second intercepting means to transfer the refrigerant gas contained in the analysis chamber to said first or, alternatively, to said second reservoir for recovering the refrigerant gas, on the basis of the outcome of said comparisons.

10. A refrigerant gas recharging/recovery station able to recharge/recover a refrigerant gas in an automotive air conditioning system characterized in that it comprises a gas analyzer system according to claim 1.

\* \* \* \* \*